(12) United States Patent
Leonard et al.

(10) Patent No.: US 6,228,120 B1
(45) Date of Patent: May 8, 2001

(54) SURGICAL EQUIPMENT FOR IMPLANTING A TOTAL SHOULDER PROSTHESIS, AND TOTAL SHOULDER PROSTHESIS CONSTITUTING SAME

(76) Inventors: Alain Leonard, 6 rue des Pyrénées, 65500 Caixon; Pierre Flurin, 15 impasse Saint Amand, 33000 Bordeaux, both of (FR)

( * ) Notice: Subject to any disclaimer, the term of this patent is extended or adjusted under 35 U.S.C. 154(b) by 0 days.

(21) Appl. No.: 09/380,709

(22) PCT Filed: Jan. 5, 1999

(86) PCT No.: PCT/FR99/00007

§ 371 Date: Sep. 8, 1999

§ 102(e) Date: Sep. 8, 1999

(87) PCT Pub. No.: WO99/34756

PCT Pub. Date: Jul. 15, 1999

(30) Foreign Application Priority Data

Jan. 9, 1998 (FR) .................................................. 98 00146

(51) Int. Cl.⁷ .................................. A61F 2/40; A61F 2/30
(52) U.S. Cl. ..................................... 623/19.12; 623/18.11; 623/19.11
(58) Field of Search .............................. 623/18.11, 19.11, 623/19.12, 19.13, 19.14

(56) References Cited

U.S. PATENT DOCUMENTS

| | | | |
|---|---|---|---|
| 3,978,528 | * | 9/1976 | Crep .................................. 623/19.12 |
| 4,003,095 | * | 1/1977 | Gristina .............................. 623/19.12 |
| 4,040,131 | * | 8/1977 | Gristina .............................. 623/19.12 |
| 5,358,526 | * | 10/1994 | Tornier ................................... 623/19 |

* cited by examiner

*Primary Examiner*—Gene Mancene
*Assistant Examiner*—Michael B. Priddy
(74) *Attorney, Agent, or Firm*—Young & Thompson (57) ABSTRACT

The invention concerns a surgical equipment provided with a total shoulder prosthesis comprising a hemispherical plate cap (20) and a prosthesis shank consisting of a humeral rod (1), a humeral plate (9) and a member (16) mutually locking the humeral rod and plate, with hemispherical contact surface (10a, 10b, 18) capable of allowing the humeral plate (9) of oscillating in all directions relative to the humeral rod (1), when the locking member (16) is in an unlocked position, and in locking the humeral rod and plate in the desired relative position.

8 Claims, 9 Drawing Sheets

ND STAGE OF INTERNATIONAL# SURGICAL EQUIPMENT FOR IMPLANTING A TOTAL SHOULDER PROSTHESIS, AND TOTAL SHOULDER PROSTHESIS CONSTITUTING SAME

CROSS REFERENCE TO RELATED APPLICATION

This is the 35 USC 371 national stage of international application PCT/FR 99/00007 filed on Jan. 5, 1999, which designated the United States of America.

FIELD OF THE INVENTION

The invention concerns a surgical device for the implantation of a total shoulder prosthesis. It covers a total shoulder prosthesis of the type including a prosthesis stem designed to be implanted in the humeral canal of a patient and a head intended to fit the prosthetic socket of the shoulder or the glenoid cavity of the patient.

BACKGROUND OF THE INVENTION

Initially, the first shoulder prostheses, so-called NEERs, consisted of monobloc prostheses, i.e., they comprised a prosthesis stem and a head in a single piece. However, experience has shown that such prostheses have two major disadvantages.

As a matter of fact, and in the first place, the one-piece nature of these prostheses requires a large inventory of different implants that can adapt to the anatomical requirements of various patients. Furthermore, since the relative position of the head and the prosthesis stem are fixed, and also because of the one-piece nature of the prosthesis, the only solution available to the practitioner in order to accurately reproduce the anatomy of the upper end of the humerus consists of fitting the humerus to the prosthesis, an operation that proves to be quite tricky and a source of failures, or at least future traumatisms, for the patient.

Several solutions have been proposed to mitigate these disadvantages, as described in particular in French patents FR-2 685 633, FR-2 727 002, FR-2 727 857, and FR-2 731 612, aimed at providing prostheses with heads and prosthesis stems linked through connecting devices whose relative position can be adjusted by rotating the head around two or three axes of rotation with respect to the prosthesis stem, then locking these elements in the desired configuration.

Compared to the NEER prostheses, these prostheses have the advantage of making it possible to approximate the exact anatomy of the upper end of the humerus. However, they also have two major disadvantages.

As a matter of fact, and in the first place, due to the design of the systems for the related locking of the head and the prosthesis stem, they first require that the practitioner uses trial prostheses in order to determine the ideal relative positioning of the head and the prosthesis stem, and then duplicates the geometry of the trial prosthesis in order to construct the final prosthesis that is to be implanted.

But this surgical technique leads to an increase in the length of the operation during which the patient is under anesthesia. Furthermore, it can be the source of errors prejudicial to the patient during the duplication of the trial prosthesis, which must be done during the operation, i.e., as quickly as possible. It should also be noted that due to the obligation of duplicating the trial prosthesis, any increased possibility of adjustment that would advantageously make it possible to provide a better reproduction of the anatomy of the upper end of the humerus leads to complicating the step of duplicating this test prosthesis. Thus, it appears in particular that this duplication step is most difficult for the prostheses described in patents FR-2 727 002 and FR-2 727 857, which offer the best-performing range of adjustments.

The second disadvantage of these prostheses results from the fact that anatomical studies have made it possible to reveal the existence of a double eccentricity, called combined offset, between the proximal metaphysical axis of the humerus and the parallel axis that passes through the center of the humeral head. This combined offset has a medial component, called medial offset, that is relatively constant from one individual to another, and a posterior component, called posterior offset, that is relatively variable from one individual to another, between which there is no relationship. And none of the current prostheses as described in particular in the aforesaid French patents makes it possible to adjust the medial offset and the posterior offset independently, so that an exact reproduction of the upper end of the humerus cannot be achieved to this day. Furthermore, this impossibility of independent adjustment of the two offsets may lead the practitioner to artificially increase the humeral retro-torsion during implantation.

SUMMARY OF THE INVENTION

The purpose of this invention is to mitigate the disadvantages of the current shoulder prostheses and its primary objective is to provide a shoulder prosthesis offering multiple continuous adjustments of the position of the head relative to the prosthesis stem, in which said prosthesis stem can be sealed directly without using trial prostheses.

Another objective of the invention is to provide a shoulder prosthesis that permits continuous independent adjustments of the medial offset and the posterior offset.

To that end, the invention first involves a surgical device comprising:
  a shoulder prosthesis stem with a humeral rod and a
    metaphysical section angled in relation to said humeral
    rod that has an upper frontal face inclined in relation to
    the humeral rod, in which a hemispherical cavity centering on an axis ($\alpha$) is provided, and a tapped bore
    opening into the bottom of the hemispherical cavity and
    centered on axis ($\alpha$),
  a humeral plate comprising:
    a hollow hemispherical ball joint with an axis of
      rotation D, featuring an external face made to fit the
      cavity of the prosthesis stem, and an internal face
      that defines a hemispherical bearing and has an
      axially drilled tapered bore,
    a tapered swivel with an axis of rotation D', eccentric
      by a distance d in relation to axis D, connected to the
      ball joint through a connecting section with a cross-
      section no larger than the maximum cross-section of
      the ball Joint, which tapered swivel and connecting
      section have a through hole drilled through them into
      the extension of the ball joint cavity,
  a locking unit comprising the following, arranged axially:
    a rod with a threaded lower section and a diameter
      matching that of the bore of the prosthesis stem and
      smaller than the minimum diameter of the tapered
      bore of the humeral plate ball joint,
    a hemispherical ball joint made to fit the hemispherical
      portion of the humeral plate ball joint,
    and a screw head for the locking unit.
  the hemispherical cavities in the prosthesis stem, the
    external and internal faces of the humeral plate ball
    joint, and the locking unit ball joint being concentric
    around a point O when the locking unit is in locked
    position, a head with a concave upper wall designed to fit the glenoid cavity of the shoulder and a lower wall with a tapered recess of a shape that matches the tapered swivel, a so-called trial head comprising a lower wall of the same size as that of the lower wall of the cap with a tapered recess of a shape that matches that of the tapered swivel, and an upper wall with a hole drilled in it that opens into said recess.

(Note that ball joints and hemispherical bearings are understood to mean components of a general hemispherical shape defining an arc of circle equal to or slightly greater than 180°.)

According to the invention, the surgical device comprises first a shoulder prosthesis stem whose component elements, humeral stem, humeral plate, and unit for related locking of said humeral rod and humeral plate have hemispherical contact bearings and are designed and arranged so that the ball joints of the humeral plate and the locking unit can oscillate in all directions around a point 0 representing the center of the hemispherical cavity in the humeral rod. This surgical device also includes trial heads with a bottom wall of the same dimensions as those of the permanent caps and designed to make it possible to adjust the position of the humeral plate and to lock the locking unit, thereby locking the humeral plate in the desired position in relation to the humeral stem.

Such surgical device first has the advantage of making it possible to directly seal the final prosthesis stem and to make adjustments in the head position using specific trial heads once this seal is made. In effect, it is therefore not necessary to use trial stems that have to be duplicated, and thereby simplifies the surgical intervention and reduces its duration.

In addition, this surgical device makes it possible to continuously adjust the inclination of the head, the retroversion, and the combined offset. In effect:

adjustments of the retroversion and the inclination are achieved through the joint made up of the hemispherical cavity in the prosthesis stem and the ball joint of the humeral plate, permitting variations in the orientation of said humeral plate centered on point 0, adjustments of the combined offset are achieved as a result of the eccentricity d between the axis of rotation D of the humeral plate ball joint and the axis of rotation D' of the humeral plate swivel.

According to another feature of the invention, the heads have an axis of rotation D' that is eccentric by a distance d' in relation to the axis of rotation D' of the tapered swivel of the humeral plate.

This arrangement makes it possible to independently adjust the notions of posterior offset and medial offset and thereby leads to achieving optimum head overlap on the bone resection.

In effect, eccentricities d, d' make it possible to give to the trial head axis D" a satellite movement relative to the axis of the humeral stem and to obtain a fine, continuous, and above all independent adjustment of the notions of medial and posterior offsets.

According to another feature of the invention, the surgical device includes a gripper equipped with a handle and a gripping head that is angled with respect to said handle, said gripping head being designed to blank off the cavity in the metaphysical section of the prosthesis stem, and comprising:

a locking unit with a threaded rod that screws into the tapped bore in the metaphysical section of the prosthesis stem, a ring mounted around said gripping head that can oscillate around a point O' on axis ($\alpha$) located at a distance from the bottom of the cavity in the prosthesis stem that is less than the distance between point O and the bottom of the cavity.

Such a gripper is designed to be rigidly assembled, using the locking unit, to the prosthesis stem without the humeral plate, in order to permit the insertion of the latter into the humeral canal.

In addition, this gripper is designed, particularly as a result of the position of point O' around which the ring oscillates, offset in relation to point O, in order to make it possible to implant the prosthesis stem so that its metaphysical section has the optimum position, guaranteeing the subsequent possibility of making the adjustments permitted by the articulated connections of the prosthesis.

Lastly, the gripping head of this gripper that blanks off the hemispherical cavity in the prosthesis stem prevents any cement from entering the cavity when the prosthesis stem is sealed in place.

According to another feature of the invention, the gripper's gripping head comprises:

a hollow cap designed to cover the front face of the prosthesis stem, that has an internal cavity forming a hemispherical bearing, and an upper wall with an axially drilled hole, and a side wall with longitudinal oblong openings, a ball joint housed in the internal cavity of the cap, with an axially drilled bore of a diameter larger than that of the tapped bore drilled in the prosthesis stem, and connecting elements between the ball joint and the ring arranged so as to extend through the oblong openings in the cap and permit angular movements of said ball joint and ring.

the locking unit consisting of a screw with a shaft made to extend through the opening in the cap and the ball joint bore.

The surgical device according to the invention further advantageously includes a set of humeral plates with connecting sections of various heights.

In effect, this set of humeral plates offers the possibility of making a translation adjustment in order to possibly restore the normal length of the humerus, an adjustment that can furthermore be refined by conventionally using a set of heads of different thicknesses.

According to another feature of the invention, the trial heads have a knurled gripping head bounding the tapered recess that has an open upper wall and an external circular ring extending around the base of said knurled head.

The invention extends to a shoulder prosthesis comprising:

a shoulder prosthesis stem with a humeral stem and a metaphysical section angled in relation to said humeral stem, with an upper front face inclined in relation to the humeral stem, in which a hemispherical cavity centered on an axis ($\alpha$) is provided, and a tapped bore opening into the bottom of the hemispherical cavity and centering on the axis ($\alpha$), a humeral plate comprising:

a hollow hemispherical ball joint with an axis of rotation D, an external face designed to fit the cavity in the prosthesis stem, and an internal face defining a hemispherical bearing, and perforated with an axially drilled tapered hole, a tapered swivel having an axis of rotation D' eccentric by a distance d in relation to axis D, connected to the ball joint through a connecting section with a cross-section no larger than the maximum cross-section of said ball joint, which tapered swivel and connecting section have a through hole drilled through them that extends into the extension of the ball joint cavity, a locking unit comprising the following, arranged axially:
a rod with a threaded lower section and with a diameter matching that of the bore in the prosthesis stem and smaller than the minimum diameter of the tapered bore of the ball joint of the humeral plate,
a hemispherical ball joint made to fit the hemispherical portion of the humeral plate ball joint,
and a screw head for said locking unit.

the hemispherical cavities in the prosthesis stem, the external and internal faces of the humeral plate ball joint, and the locking unit ball joint being concentric around a point O when the locking unit is in locked position, a cap with a concave upper wall made to fit the shoulder socket and a lower wall with a tapered recess whose shape matches the tapered swivel.

In addition, the cap advantageously has an axis of rotation D" that is eccentric by a distance d from the axis of rotation D' of the tapered swivel of the humeral plate.

BRIEF DESCRIPTION OF THE DRAWINGS

Other features, purposes, and advantages of the invention will become evident from the following detailed description referring to the attached drawings, which, as a non-limititative example, represent a preferred embodiment. On these drawings, which are an integral part of this description.

DETAILED DESCRIPTION OF THE INVENTION

The surgical device according to the invention represented in the figures primarily comprises a complete humeral prosthesis, a gripper designed to help implant the humeral prosthesis stem inside a humeral canal, and so-called trial heads used to adjust the reconstruction parameters of the top end of the humerus.

Conventionally, it is understood that this surgical device includes a set of prosthesis stems of various lengths and diameters. It also includes a set of heads of various diameters and heights, as well as a set of trial heads of the same diameter as said heads.

Figure 1:
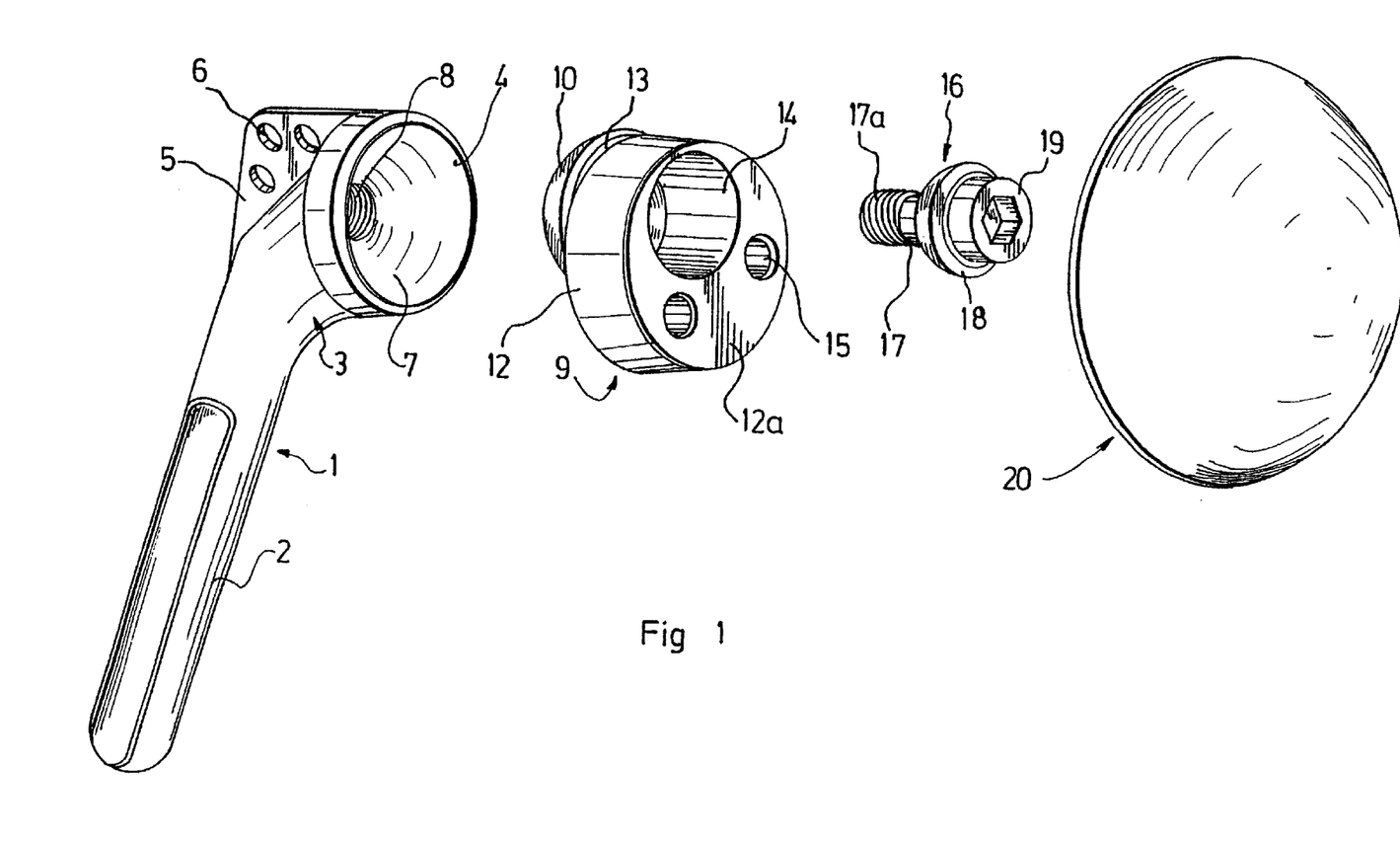
FIG. 1 is an exploded perspective view of the various component elements of a humeral prosthesis according to the invention.
Figure 2:
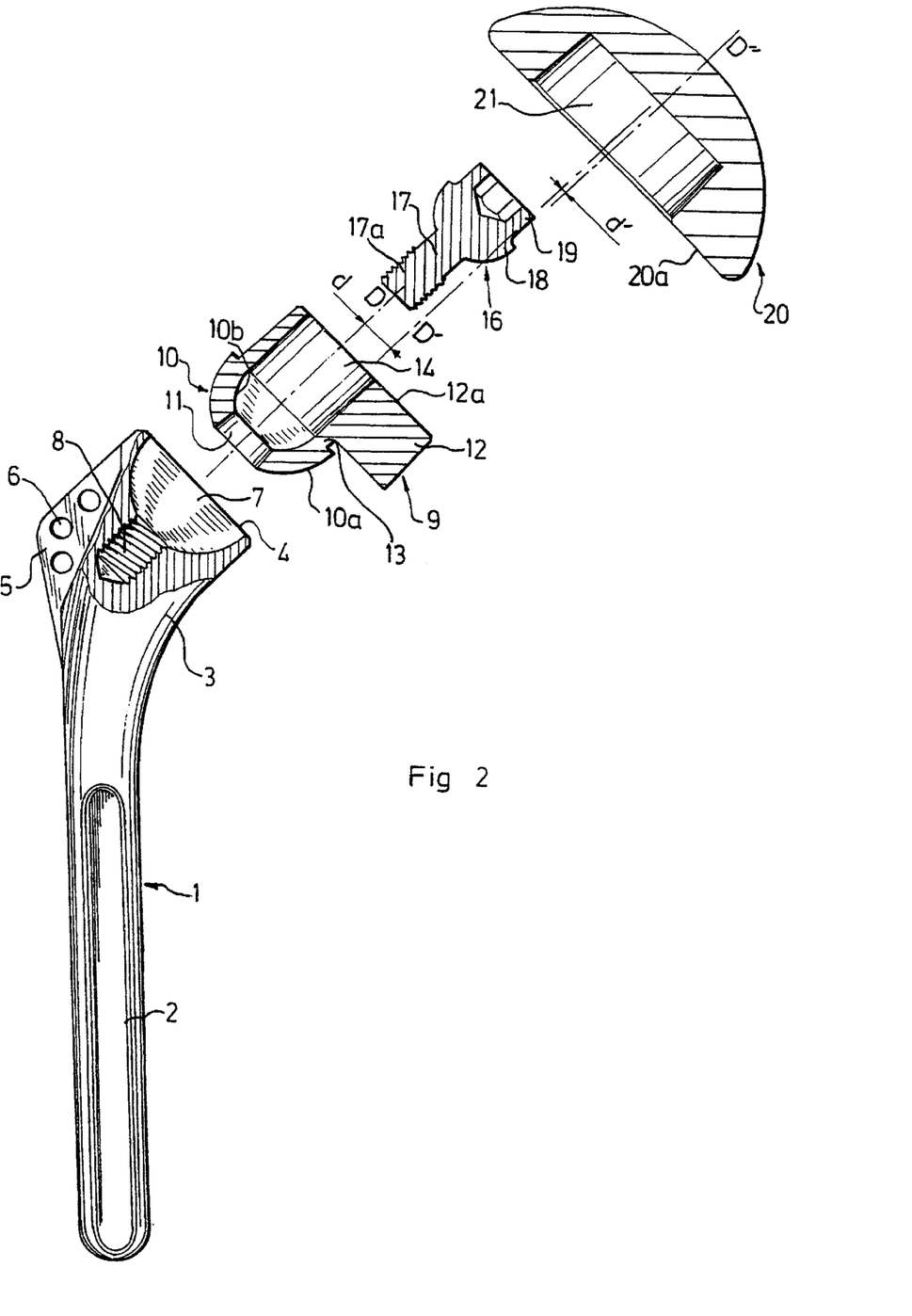
FIG. 2 is an exploded axial longitudinal section of these components with the prosthesis stem partially represented in side view.
Figure 3:
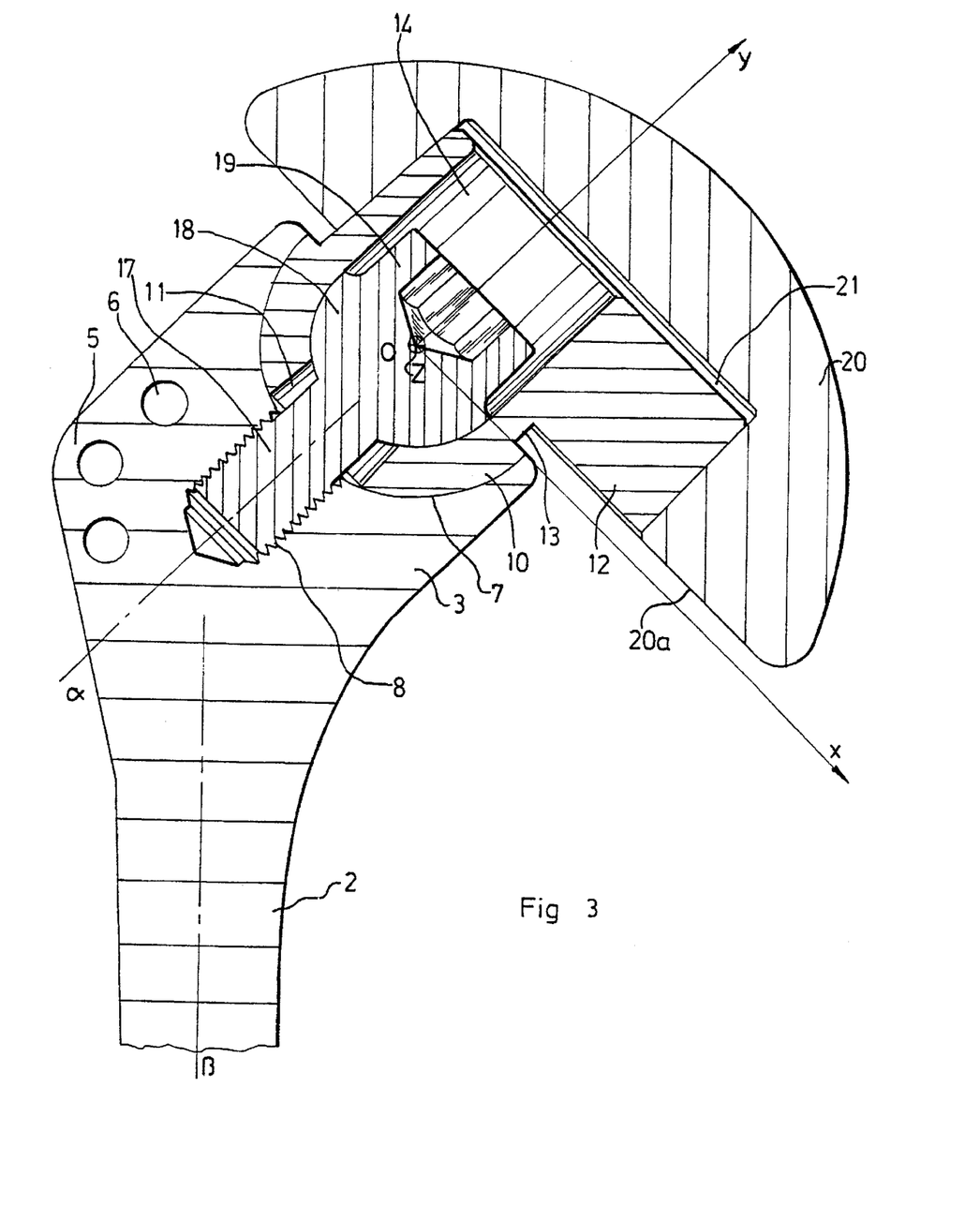
FIG. 3 is an axial longitudinal section view of this humeral prosthesis with the various component elements assembled.

The humeral prosthesis according to the invention represented in FIGS. 1 to 3 first comprises a humeral prosthesis stem 1 designed to be implanted into a patient's humeral canal.

This prosthesis stem 1 comprises also a cylindrical rod 2 and a metaphysical section 3 that has a flared profile and makes an angle in relation to the cylindrical rod 2 so as to present an upper frontal face 4 of a circular shape centered on an axis ($\beta$) that is inclined in relation to the axis ($\alpha$) of said cylindrical rod 2.

This prosthesis stem 1 also includes a fin 5 extending into the extension of the cylindrical rod 2 behind the metaphysical section 3 and provided with openings such as 6 that in case of a fracture are intended to permit the reconstruction of the upper part of the humerus around the prosthesis.

The metaphysical section 3 of this cylindrical rod 2 also has a hemispherical cavity 7 centered on axis ($\alpha$) and made from the upper frontal face 4, and a tapped bore 8, also centered on axis ($\alpha$), that opens into the bottom of said cavity 7.

The humeral prosthesis also comprises a humeral plate 9 to make the connection between the prosthesis stem 1 and the head described below.

This humeral plate 9 first comprises a hollow hemispherical ball joint 10 designed to fit the hemispherical bearing formed by the cavity 7 in the metaphysical section 3 of the prosthesis stem 1 and having for that purpose an external wall 10a of the same radius as said cavity 7, plus tolerance. Since this hemispherical ball joint 10 is hollow, it also has an internal wall 10b defining a hemispherical surface. Lastly, this hemispherical ball joint 10 has a tapered bore 11 drilled in it that centers on the axis of rotation (D) of said ball joint. This bore 11 also has a diameter that decreases from the internal wall 10a towards the external wall 10b of the ball joint, and a minimum diameter larger than that of the tapped bore 8 in the prosthesis stem 1.

The humeral plate 9 also comprises a swivel 12 of tapered shape overlying the hemispherical ball joint 10 and connected to the flat upper frontal wall of the latter through a cylindrical connecting section 13 centered on the ball joint's axis of rotation (D), having the same inside diameter as the maximum inside diameter of said ball joint 10 and an outside diameter slightly smaller than its maximum outside diameter. This swivel 12 also has an upper wall 12a in which two blind holes such as 15 are provided.

This tapered swivel 12 also has an average cross-section larger than the maximum cross-section of the hemispherical ball joint 10, in a ratio on the order of 1.3 to 1.5 times and is arranged with respect to the latter so that its axis of rotation (D') is eccentric by a distance d on the order of five millimeters in relation to said ball joint's axis of rotation (D).

In addition, the humeral prosthesis has a unit 16 for relative locking of the humeral plate 9 and the prosthesis stem 1.

This locking unit 16 first has a cylindrical rod 17 provided with a threaded bottom end section 17a designed to screw into the tapped bore 8.

This rod 17 is also topped by a hemispherical ball joint 18 designed to fit the hemispherical bearing formed by the internal face 10b of the ball joint 10 of the humeral plate 9, and for that purpose having an external wall in contact with said hemispherical bearing that has the same radius as said bearing, plus tolerance.

The locking unit 16 also has a screw head 19 coaxial with the axis of rotation of the hemispherical ball joint 18, for example of the hexagonal type, that makes it possible to lock together the locking unit, the humeral plate 9, and the prosthesis stem 1 using any appropriate tool. In addition, as shown in FIG. 3, once this lock is set, the various spherical surfaces and spherical ball joints are concentric around the same point O.

The humeral prosthesis also comprises a head 20, designed to fit the prosthetic or glenoid cavity of the shoulder and having a circular lower wall 20a in which a tapered housing 21 of a shape matching that of the tapered swivel 12, designed to cover the latter, is provided Furthermore, the axis of symmetry (D") of this head 20 is eccentric by a distance on the order of 1.5 mm from the axis of symmetry D' of the tapered swivel 12, so that the eccentricity of said axis (D") in relation to the axis of rotation (D) of the hemispherical ball joint 10 can vary within a range of distances from d–d' to d+d'.

Figure 4:
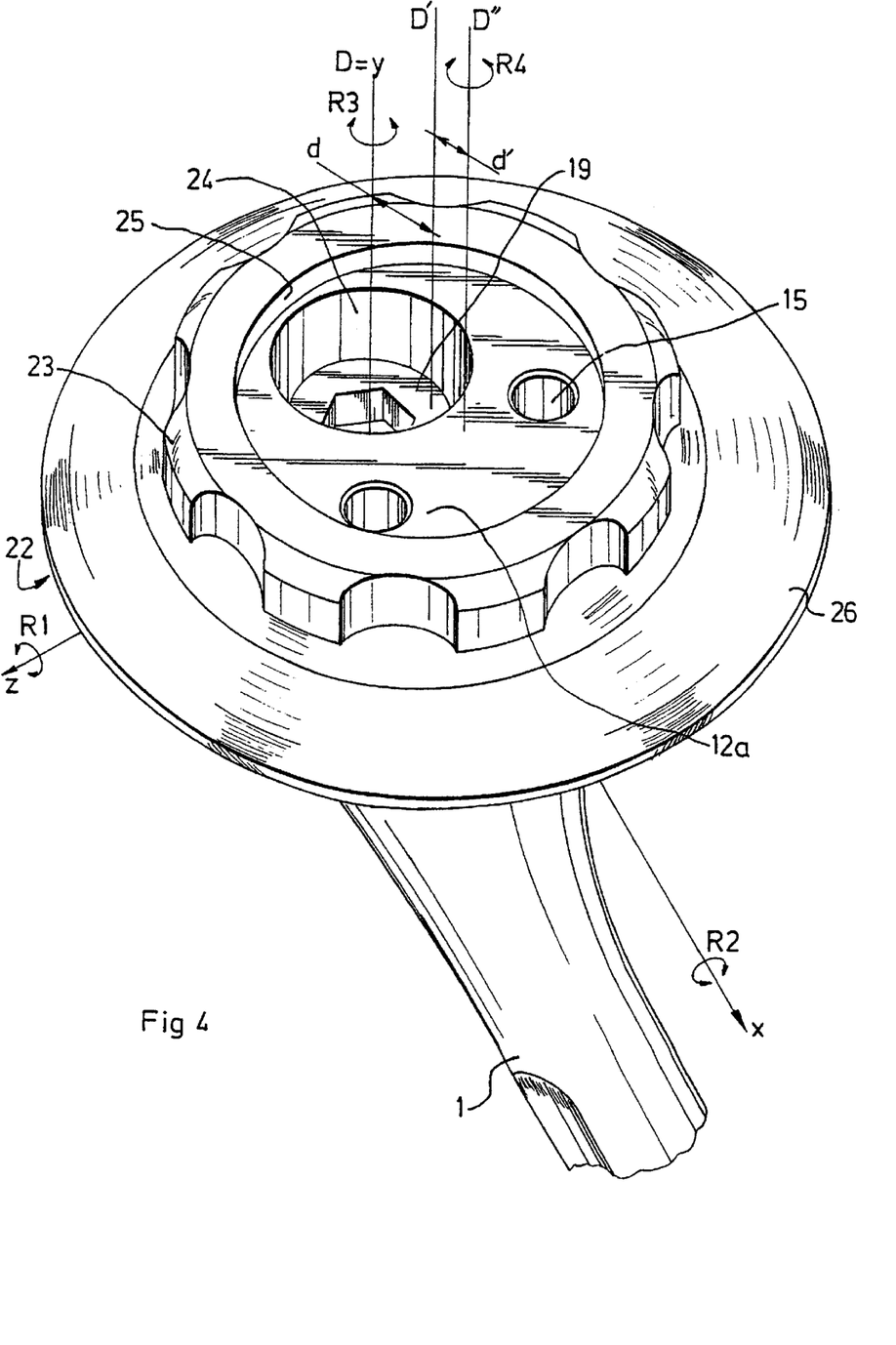
FIG. 4 is a partial perspective top view of a humeral prosthesis according to the invention, equipped with a trial head.
Figure 5:
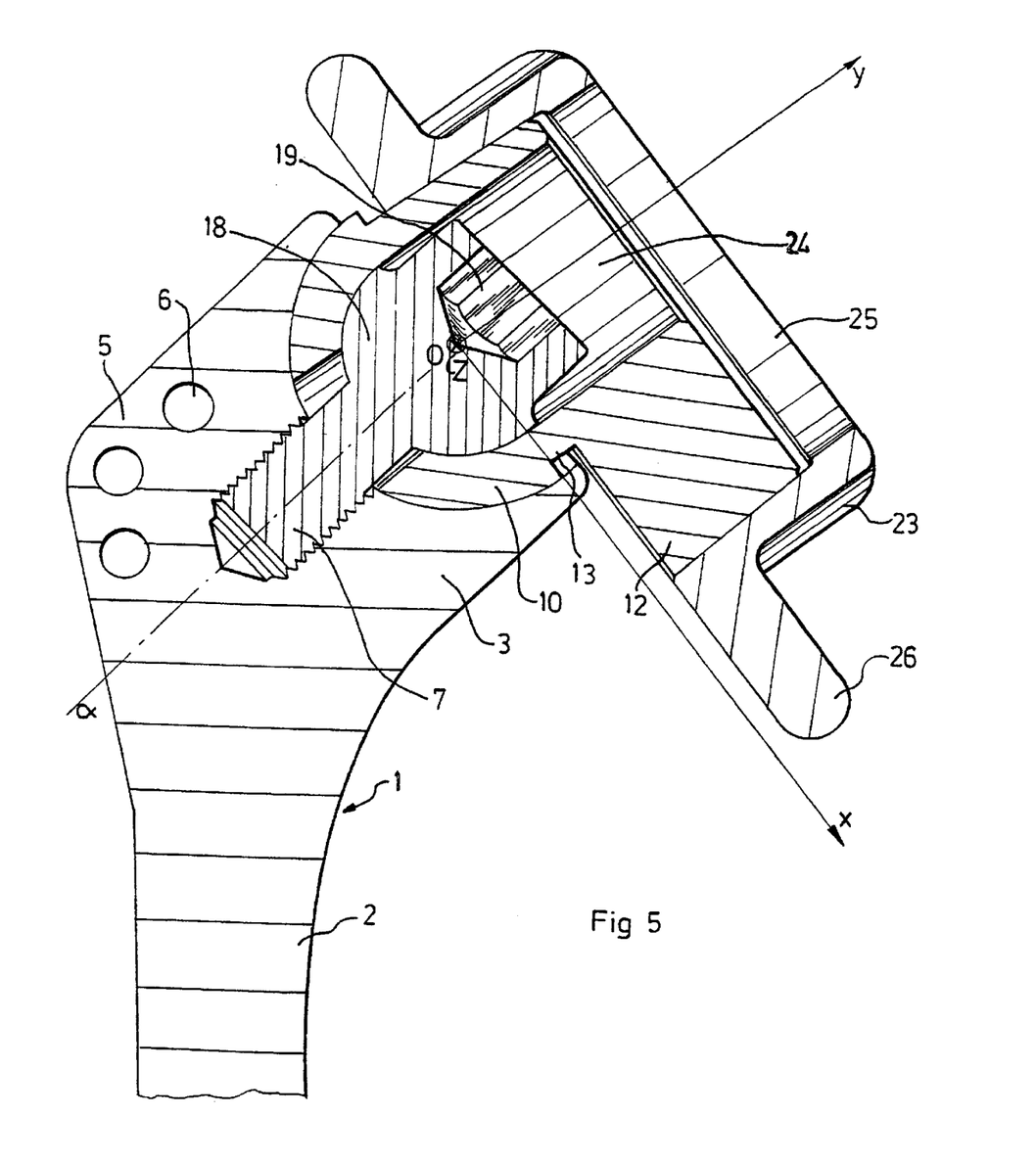
FIG. 5 is an axial longitudinal section of the humeral prosthesis in FIG. 4.
Figure 6:
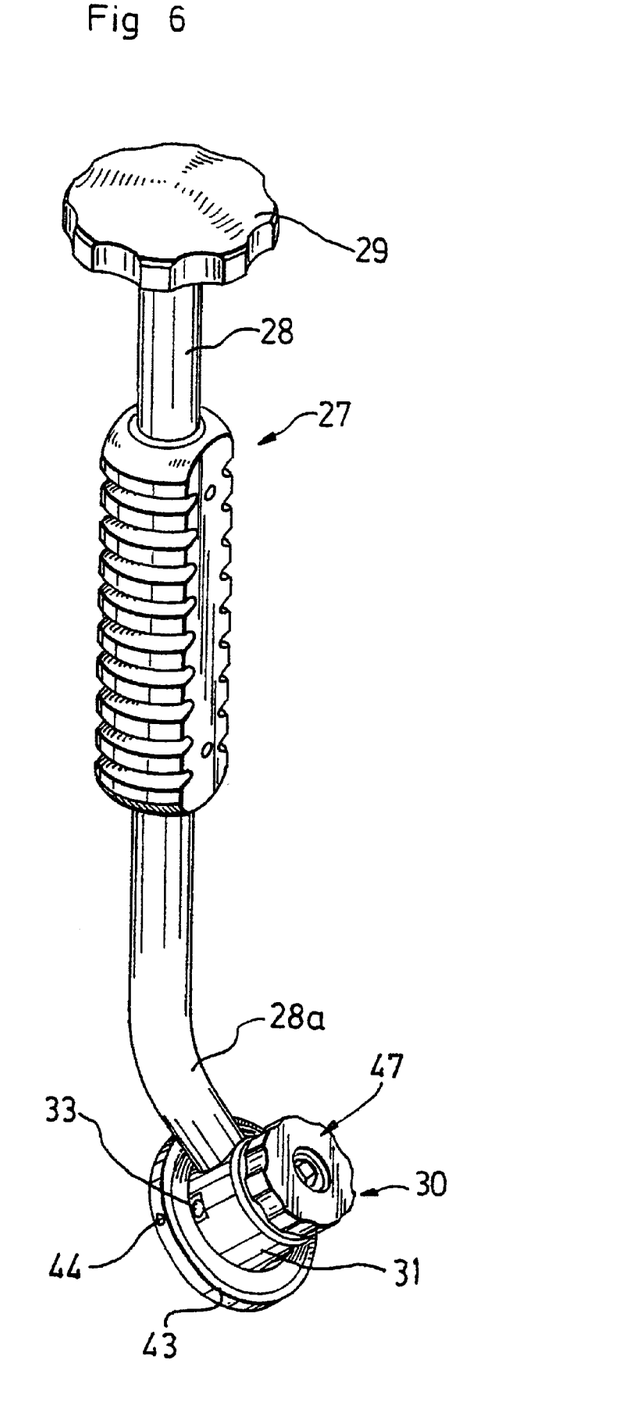
FIG. 6 is a perspective view of a gripper designed to implant a humeral prosthesis according to the invention.
Figure 7:
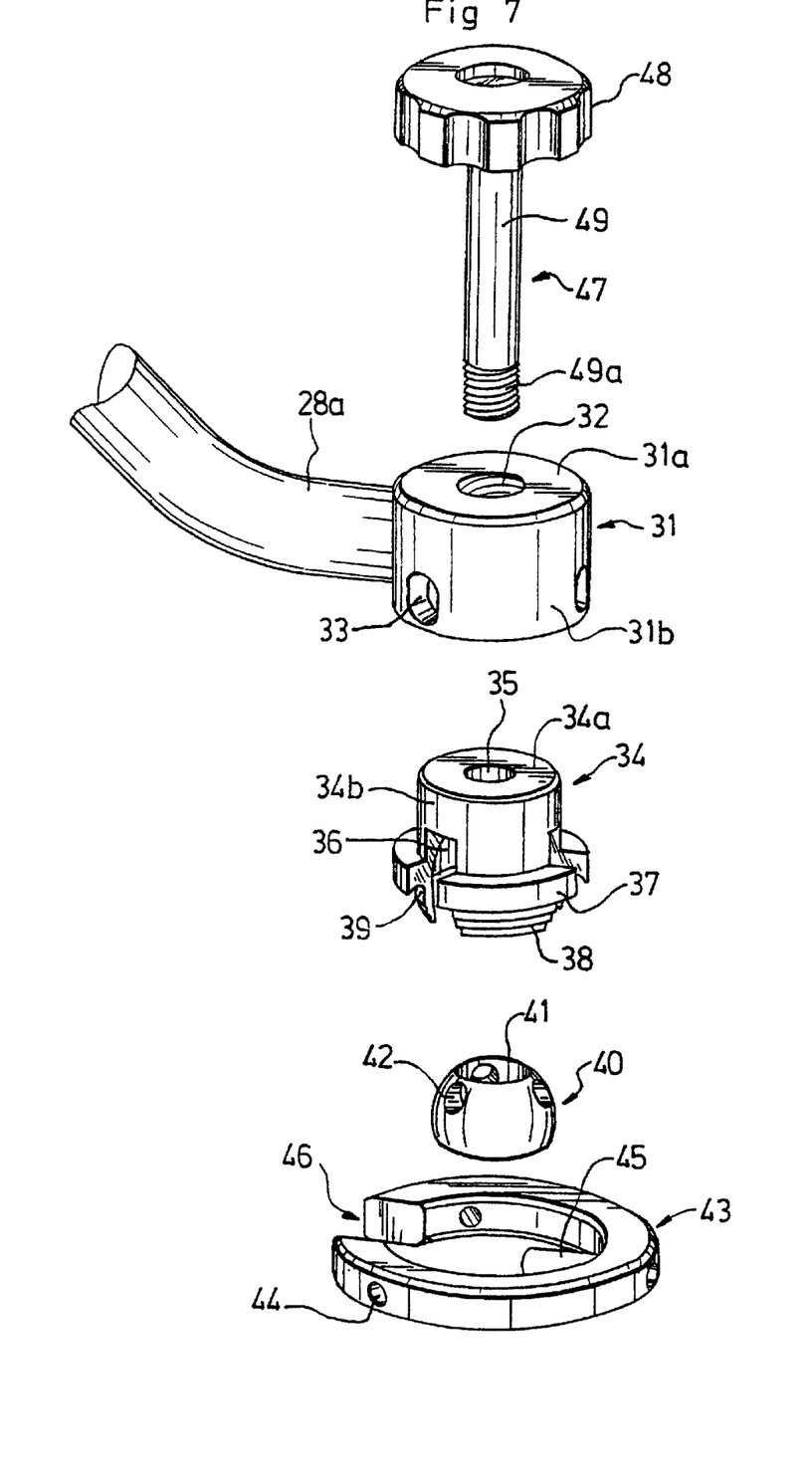
FIG. 7 is a partial perspective exploded view of the various component elements of the gripper.
Figure 8:
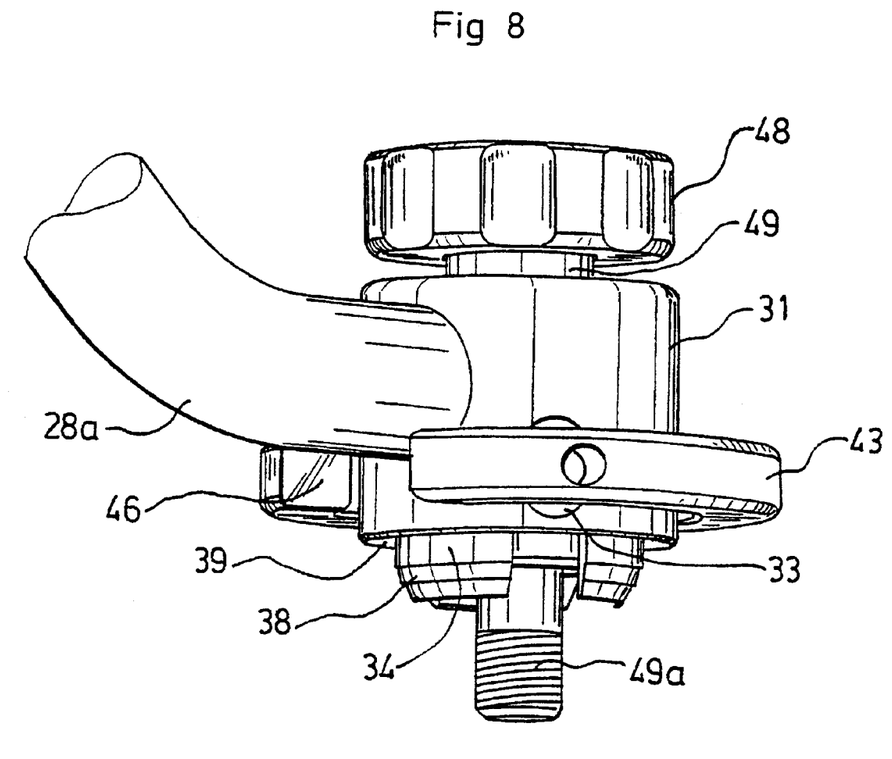
FIG. 8 is a partial perspective view of the gripper and a humeral prosthesis stem, unassembled.

The trial heads 22 shown in FIGS. 4 and 5 are designed to permit adjustments of the upper humerus end reconstruction parameters once the prosthesis stem 1 is implanted and cemented in the humeral canal.

These trial heads 22 first have a knurled hollow cylindrical gripping head 23 with an axis of rotation D" bounding a tapered housing 24 whose shape matches that of the tapered swivel 12, designed to house the latter, and having an upper face 25 that is open to permit access to the locking unit 16 once said heads are mounted on said swivels.

These trial heads 22 also have a ring 26 at the base of the gripping head 23 that has the same outside diameter as the corresponding permanent head 20.

The gripper 27 shown in FIGS. 6 to 9 has a cylindrical handle 28 with an upper gripper wheel 29 and a lower section 28a cranked by an angle to match the inclination angle of the metaphysical section 3 of the prosthesis stem 1.

This gripper also has a gripping head 30 for the metaphysical section 3 of the prosthesis stem 1 intended to fit the latter after removal of the humeral plate 9, in order to implant it in a humeral canal.

This gripping head 30 first has a cylindrical cap 31 made of metallic material, integral with the lower end 28a of the handle 28, that has an upper wall 31a with an axially drilled circular hole 32, a lateral wall 31b opposite the upper wall 31a perforated with three oblong holes such as 33 uniformly distributed around the axis of the casing, and an open lower face.

This gripping head 30 also has a generally cylindrical internal liner 34 made of plastic, having a shape permitting it to be force-fitted into the cap 31. This inside liner 34 first has an upper wall 34a with an axially drilled circular opening 35 and a side wall 34b with three notches such as 36 arranged so that they are facing the oblong openings 33 in the cap 31.

This inside liner 34 also has a lower peripheral rim 37 designed out to butt against the lower edge of the cap 31, with slots facing the notches 36 in the cap. It also has an internal cavity forming a hemispherical bearing extended by an incurved bottom skirt 38 giving to the hemispherical bearing a retaining function. Lastly, this inside lining 34 has an annular groove 39 with a nosed cross-section shaped to cover the upper edge of the hemispherical cavity 7 in the prosthesis stem 1, located on the underside of the peripheral rim 37.

The gripping head 30 also has a truncated spherical ball joint 40 made of metallic material sized so as to fit into the inside liner 34 This ball joint 40 first has a longitudinal bore 41 with a diameter larger than that of openings 32, 35 in the cap 31 and the inside liner 34. It also has three radial openings such as 42 evenly distributed around the axis of symmetry of the ball joint 40, located so that each is opposite an oblong opening 33 in the cap 31.

The gripping head 30 also has a ring 43 made of plastic whose inside diameter fits around the peripheral rim 37 of the inside liner 34. This ring 43 has three evenly distributed radial holes such as 44 located so as to make it possible to make it integral with the spherical ball joint 40 using metal pins such as 45 which extend through the oblong openings 33 in the cap 31 and the notches 36 in the inside liner 34. These pins 45 also have a diameter smaller than the size of the oblong holes 33 in order to permit angular movements of the ring 43 and the ball joint 40 relative to the inside liner 34 and the cap 31. In order to permit such angular movements, the ring 43 has an opening 46 located so as to be positioned opposite the bent end 28a of the handle 28.

Lastly, the gripping head 30 contains a screw 47 with a knurled head 48 and a cylindrical shaft 49 with a threaded lower end 49a and a diameter that fits through the openings 32, 35 in the cap 31 and the lining 34 and the bore 41 in the ball joint 40, and screws into the tapped bore 8 of the prosthesis stem 1.

Such a gripper 27 is suited to be assembled rigidly with the prosthesis stem 1 so as to permit the insertion of said stem into a humeral canal. It is also designed to cover the hemispherical cavity 7 of this prosthesis stem 1 so as to prevent any cement from entering this cavity 7.

Figure 9:
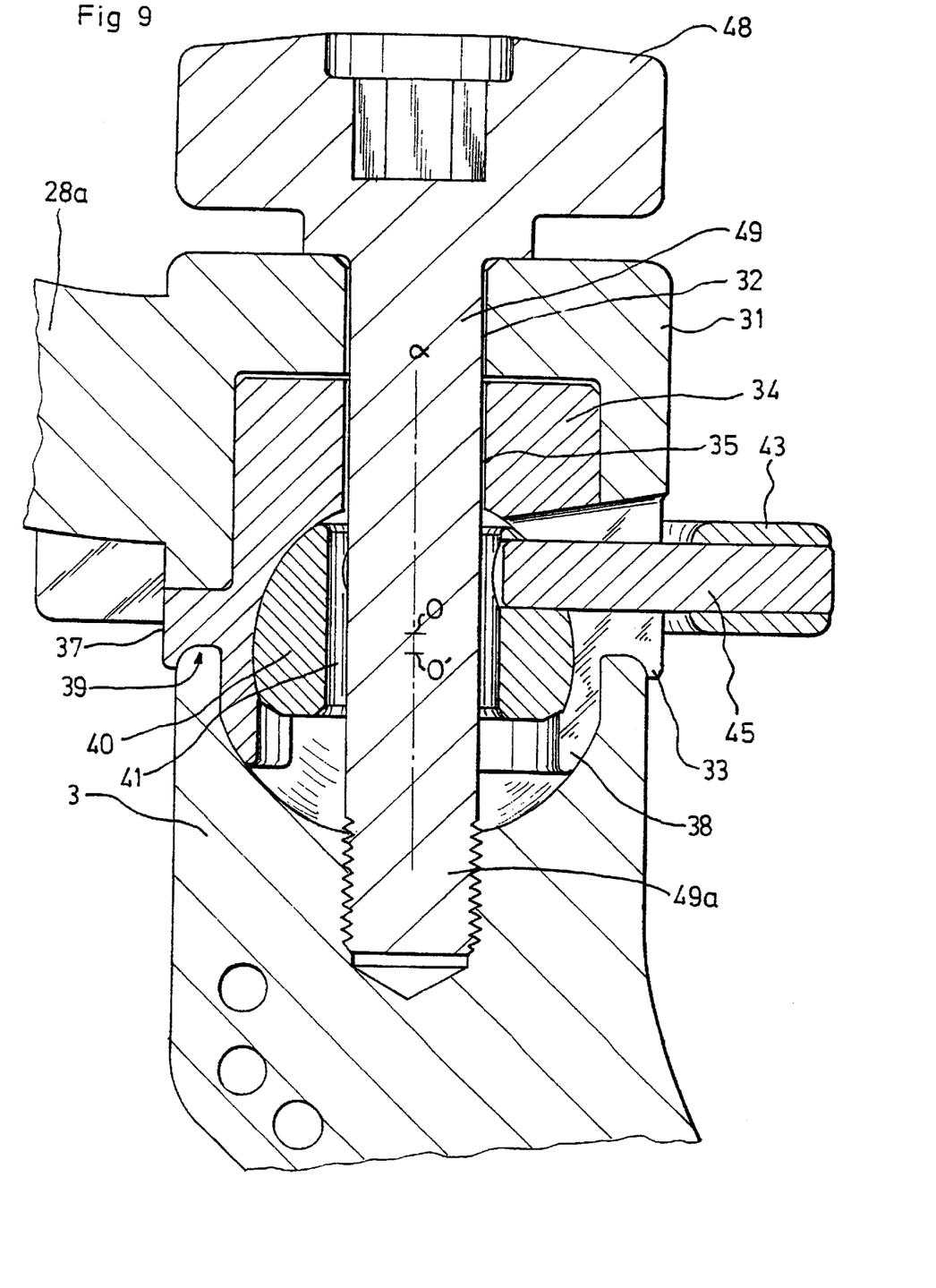
FIG. 9 is an axial longitudinal section of a gripper and a humeral prosthesis stem, assembled.

The dimensional characteristics of the various components of this gripper are also so that:
    the amplitude of oscillation of the ring 42, as defined by the height of the oblong holes 33, represents the amplitude of the adjustments permitted by the humeral plate, described in detail below,
    as shown in FIG. 9, the center of rotation O' of the ball Joint 40 is offset downwards by a distance on the order of one mm in relation to the center O of concentricity of the hemispherical bearings and ball joints of the prosthesis.

Provided these requirements are met, such a gripper 27 makes it possible to implant the prosthesis stem 1 in a humeral canal so that its metaphysical section 3 is optimally positioned and, particularly as a result of the offset between centers O and O', guarantees the subsequent possibility of making all the adjustments permitted by the articulated connections of the prosthesis.

The following are the various steps for implanting a prosthesis using the surgical device described above.

First, the gripper 27 is fastened to the prosthesis stem 1 and the stem is inserted in the canal of the humerus, the head of which has been cut off conventionally beforehand, until the ring 43 butts against the bone resection. At this stage, the prosthesis stem 1 can be permanently sealed using cement that has previously been injected into the canal with the excess being forced out.

The gripper 27 is then removed and the humeral plate 9 put into place using the locking unit 16, which is not fully screwed so as to allow rotation of the ball joint 10 inside the hemispherical cavity 7.

A trial head 22 of adequate diameter is then positioned on the tapered swivel 12 and the operator can recreate the geometry of the upper end of the humerus using the various adjustments available to him, which can be broken down into four elementary rotations:
    a rotation R1 having a center O around an axis Oz, which makes it possible to incline the humeral plate 9 and therefore the cap 22 with respect to the axis (β) of the prosthesis stem 1, a rotation R2 having a center O around an axis Ox that allows adjustment of the retroversion of the cap 22, a rotation R3 having a center O around an axis Oy which, in association with the eccentricity (d) between the axes D and D', permits a preliminary adjustment of the combined offset, and a rotation R4 around the axis D" which, in association with the eccentricity (d') between the axes D' and D" permits a second adjustment of the combined offset independently of the adjustment resulting from rotation R3.

Note that rotations R3 and R4 make it possible to describe a satellite movement in the center of the cap 22 with respect to the axis (β) of the prosthesis stem 1 that leads to a refined, continuous, and above all independent adjustment of the notions of medial offset and posterior offset.

The operator can also make a translation adjustment along axis Oy in order to possibly restore the normal length of the humerus. To that end, a set of humeral plates 9 with connecting sections 13 of various heights may also be provided in addition to the caps 20 of various thicknesses.

Once the optimum positioning has been achieved, the operator may then proceed with locking using the locking unit 16 accessible through the open face 25 of the trial head 22, the tapered swivel 9 preferably being held in position by means of an instrument of any known type having two prongs arranged to be inserted into the blind holes 15 of the tapered swivel 12.

Locking the locking unit 16 leads to the exertion of a radial pressure of the hemispherical ball joint 16 against the hemispherical bearing 10b of the humeral plate 9, and thereby locks the humeral plate 9 in the desired position relative to the prosthesis stem 1.

Lastly, the trial head 22 is removed and the permanent head 20 is put into place.

Such a surgical device design first has the advantage of making it possible to effect position adjustments of the head 20 directly on the permanent prosthesis stem 1 without having to resort to a trial implant as is now necessary, and thereby leads to a shorter operating time and decreased risks of errors.

Furthermore, it offers the possibility of making a number of independent and continuous adjustments that lead to a very accurate reconstruction of the humeral anatomy.

What is claimed is:

1. A surgical device for the implantation of a total shoulder prosthesis, the device comprising:
    a shoulder prosthesis stem with a humeral rod and a metaphysical section angled in relation to said humeral rod and presenting an upper frontal face centered on an axis and inclined in relation to the humeral rod; said metaphysical section having a hemispherical cavity centered on said axis, and a tapped bore opening into the bottom of the hemispherical cavity and also centered on said axis;
    a humeral plate comprising:
        a hollow hemispherical ball joint having an axis of rotation and comprising an external face made to fit the cavity in the prosthesis stem and an internal face that defines a hemispherical bearing and has an axially drilled tapered bore;
        a tapered swivel having an axis of rotation eccentric by a distance d in relation to the axis of rotation of the ball joint; said tapered swivel being connected to the ball joint through a connecting section having a cross-section no larger than the maximum cross-section of said ball joint; the tapered swivel and connecting section having a through hole drilled through them that extends into the extension of the cavity of the ball joint;
    a locking unit comprising the following, arranged axially:
        a rod having a threaded lower section and a diameter matching that of the tapped bore in the prosthesis stem and smaller than the minimum diameter of the tapered bore in the ball joint of the humeral plate;
        a hemispherical ball joint made to fit the hemispherical portion of the ball joint of the humeral plate; and
        a screw head for the locking unit;
    the hemispherical cavity in the prosthesis stem, the external and internal faces of the ball joint in the humeral plate, and the ball joint of the locking unit being concentric around a point O when the locking unit is in locked position;
    a head with a concave upper wall designed to fit a shoulder socket and a lower wall with a tapered housing having a shape that matches the tapered swivel; and
    at least one trial head comprising a lower wall having the same size as that of the lower wall of the head with a tapered recess having a shape that matches that of the tapered swivel and an upper wall with a hole drilled therethrough that opens into said recess.

2. The surgical device according to claim 1, further comprising a gripper with a handle and a gripping head that is angled with respect to the handle; said gripping head being designed to blank off the cavity in the metaphysical section of the prosthesis stem, and comprising:
    a locking device with a threaded rod that screws into the tapped hole in the metaphysical section of the prosthesis stem;
    a ring mounted around said gripping head that can oscillate around a swivel point O' on the axis located at a distance from the bottom of the cavity in the prosthesis stem that is less than the distance between point O and the bottom of the cavity.

3. The surgical device according to claim 2, wherein the gripping head of the gripper comprises:
    a hollow cap for covering the front face of the prosthesis stem; said cap having an internal cavity forming a hemispherical bearing, an upper wall with an axially drilled hole, and a side wall with lengthwise oblong openings;
    a ball joint housed in the internal cavity of the cap with an axially drilled hole of a diameter larger than that of the tapped bore of the prosthesis stem; and
    connecting elements between the ball joint and the ring arranged so as to extend through the oblong openings in the cap and permit angular movements of said ball joint and ring;
    the locking device comprising a screw with a shaft made to extend through the opening in the cap and the bore of the ball joint.

4. The surgical device according to claim 1, wherein the head and the cap have an axis of rotation eccentric by a distance d' in relation to the axis of rotation of the tapered swivel of the humeral plate.

5. The surgical device according to claim 1, further comprising a set of humeral plates with connecting sections of various heights.

6. The surgical device according to claim 1, wherein the trial head has a knurled gripping head bounding the tapered recess that has an open upper wall and an external circular ring extending around a base of said knurled head.

7. A total shoulder prosthesis comprising in combination:
- a shoulder prosthesis stem with a humeral rod and a metaphysical section angled in relation to said humeral rod, with an upper front face inclined in relation to the humeral rod; said metaphysical section having a hemispherical cavity centered on an axis, and a tapped bore opening into the bottom of the hemispherical cavity and centering on the axis;
- a humeral plate comprising:
  - a hollow hemispherical ball joint with an axis of rotation, with an external face designed to fit the cavity in the prosthesis stem and an internal face defining a hemispherical bearing, and perforated with an axially drilled tapered bore;
  - a tapered swivel having an axis of rotation eccentric by a distance d in relation to the axis of rotation of the ball joint, said tapered swivel being connected to the ball joint through a connecting section having a cross-section no larger than the maximum cross-section of said ball joint; the tapered swivel and connecting section having a through hole drilled through them that extends into the extension of the cavity in the ball joint;
- a locking unit comprising the following, arranged axially:
  - a rod having a threaded lower section and a diameter matching that of the tapped bore in the prosthesis stem and smaller than the median diameter of the tapered bore of the ball joint of the humeral plate;
  - a hemispherical ball joint made to fit the hemispherical part of the ball joint of the humeral plate; and
  - a screw head for said locking unit;
- the hemispherical cavity in the prosthesis stem, the external and internal faces of the ball joint of the humeral plate, and the ball joint of the locking unit being concentric around a point O when the locking unit is in locked position; and
- a head with a concave upper wall made to fit a shoulder glenoid cavity/glenoid component and a lower wall with a tapered recess whose shape matches the tapered swivel.

8. The total shoulder prosthesis according to claim 7, wherein the head has an axis of rotation eccentric by a distance d' in relation to the axis of rotation of the tapered swivel of the humeral plate.

* * * * *